United States Patent [19]

Morrison et al.

[11] 4,013,778
[45] Mar. 22, 1977

[54] METHOD FOR REDUCING BLOOD PRESSURE

[75] Inventors: Glenn C. Morrison, Dover; Wiaczeslaw A. Cetenko, Parsippany, both of N.J.

[73] Assignee: Warner-Lambert Company, Morris Plains, N.J.

[22] Filed: Sept. 29, 1975

[21] Appl. No.: 617,546

Related U.S. Application Data

[62] Division of Ser. No. 494,793, Aug. 5, 1974, Pat. No. 3,973,016.

[52] U.S. Cl. .......................... 424/251; 260/256.4 N
[51] Int. Cl.² ....................................... C07D 239/70
[58] Field of Search ............. 260/256.4 N, 239 BA; 424/251

[56] References Cited

UNITED STATES PATENTS

| | | | |
|---|---|---|---|
| 3,239,504 | 3/1966 | Brown et al. | 260/239 BA |
| 3,644,364 | 2/1972 | Anthony | 260/256.4 N |

*Primary Examiner*—Paul M. Coughlan, Jr.
*Attorney, Agent, or Firm*—Albert H. Graddis; Frank S. Chow; George M. Yahwak

[57] ABSTRACT

The present invention relates to a method for reducing blood pressure in a hypertensive mammal by the administration of a novel hydroxypyrimidine of the formula:

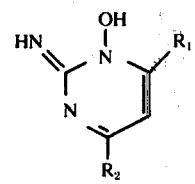

wherein $R_1$ is —$CH_3$ or —$NH_2$; and $R_2$ is

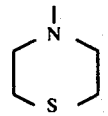

or 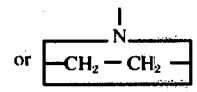 .

4 Claims, No Drawings

METHOD FOR REDUCING BLOOD PRESSURE

This is a division, of application Ser. No. 494,793 filed Aug. 5, 1974, U.S. Pat. No. 3,973,016.

Hypertension has been defined as a condition whereby there is an abnormal elevation of diastolic blood pressure. In the general population, normal and elevated blood pressures form a continuum with no set line of demarcation; nevertheless it is customary to consider a diastolic pressure of 90 mmHg as the upper limit of a normal reading. It is well known that if hypertension is not treated, it will place an extra burden on the small branches of the arterial tree and will predispose the hypertensive individual to other complications such as renal dysfunction.

The management of hypertension has as one of its objectives the lowering of the diastolic blood pressure.

Although there are many types of drugs available to lower blood pressure, each has its faults. By combining drugs that lower blood pressure by different mechanisms, additive effects can be obtained. Careful combination of drugs sometimes makes it possible to decrease the total incidence of side reactions by reducing the required dosage of an individual drug. It may even happen in some instances, that the side effects of one drug may be used to counteract those of another. For example, the tachycardia associated with hydralazine can be reduced by combined use of guanethidine which produces bradycardia, and the diarrhea caused by guanethidine can be reduced by ganglioplegic agents which induce constipation. Good control is rarely achieved with a single compound of the prior art.

The present invention relates to a method in lowering blood pressure in a hypertensive mammal by the administration of a novel 1,2-dihydro-2-imino-1-pyrimidinol of the formula:

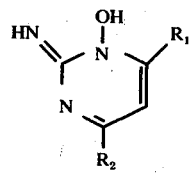

(I)

wherein $R_1$ may be a methyl or amino moiety and $R_2$ may be a thiomorphilino or, when $R_1$ is an amino moiety, $R_2$ may be a 3-azabicyclo[3.2.2]non-9-yl moiety. More particularly $R_1$ may be —CH$_3$ or —NH$_2$, and $R_2$ may be

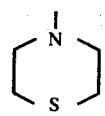

or that $R_2$ is

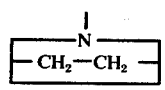

with the proviso that $R_2$ is

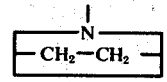

only when $R_1$ is —NH$_2$.

More particularly, the present invention is concerned with the following hydroxypyrimidines:

6-amino-1,2-dihydro-2-imino-4-thiomorpholine-1-pyrimidinol

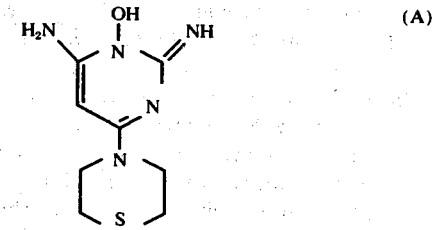

(A)

6-amino-4-(3-azabicyclo[3.2.2]non-9-yl)-1,2-dihydro-2-imino-1-pyrimidinol      3-(6-amino-1,2-dihydro-1-hydroxy-2-imino-4-pyrimidinyl)-3-azabicyclo[3.2.2-]nonane

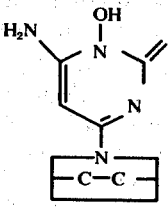

1,2-dihydro-2-amino-6-methyl-4-thiomorpholino-1-pyrimidinol

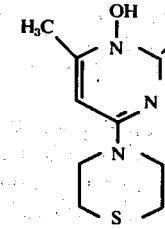

These three diaminopyrimidines possess similar pharmacological properties.

The following examples illustrate the methods contemplated by the inventors for preparing these novel hydroxypyrimidines:

EXAMPLE 1

6-AMINO-1,2-DIHYDRO-2-IMINO-4-THIOMORPHOLINO-1-PYRIMIDINOL

A mixture of 16.1 g of 6-amino-4-chloro-1,2-dihydro-2-imino-1-pyrimidinol, 32.1 g of thiomorphline, and 75 ml of dimethyl formamide is heated at 110° C in a nitrogen atmosphere for 17 hours. The solvent is removed under high vacuum. The residue is dissolved in 2 normal hydrochloric acid, and the resulting solution made basic with 5% ammonium hydroxide. There is deposited 13.0 g (57%) of a crystalline solid mp 242°(dec). Recrystallization from methanol-ethanol gives an off-white crystalline solid, mp 246° C(dec).

Anal. Calcd. for $C_8H_{13}N_5OS$: C, 42.28; H, 5.77; N, 30.81; S, 14.11. Found: C, 42.17; H, 5.81; N, 30.57; S, 14.26.

EXAMPLE 2

6-AMINO-4-(3-AZABICYCLO[3.2.2]NON-9-YL)-1,2-DIHYDRO-2-IMINO-1-PYRIMIDINOL

A mixture of 16.1 g of 6-amino-4-chloro-1,2-dihydro-2-imino-1-pyrimidinol, 32.1 g of 3 azabicyclo[3.2.2]nonane, and 200 ml of dimethyl sulfoxide are heated at 110° C in a nitrogen atmosphere for 17 hours. The reaction mixture is poured into water, filtered, made basic with 5% ammonium hydroxide solution, and extracted with chloroform. The chloroform layer is washed with water, dried over sodium sulfate and the solvent removed. Trituration with methylene chloride gives 11.7 g of a solid, mp 265°(dec). Recrystallization from methanol-ethyl acetate gives a white crystalline solid, mp 268° C(dec).

Anal. Calcd. for $C_{12}H_{19}N_5O$: C, 57.81; N, 7.68; N, 28.09. Found: C, 57.64; H, 7.80; N, 27.88.

EXAMPLE 3

1,2-DIHYDRO-2-IMONO-6-METHYL-4-THIOMORPHOLINO-1-PYRIMIDINOL

A mixture of 32 g of 4-chloro-1,2-dihydro-2-imino-6-methyl-1-pyrimidinol, 46 g of thiomorphline, and 200 ml of dimethyl sulfoxide was heated at 100° C in a nitrogen atmosphere for 17 hours. The solvent is removed under high vacuum. The residue is shaken with 5% ammonium hydroxide solution and with chloroform. The chloroform layer is washed with water, dried over sodium sulfate and the solvent removed. Trituration of the residue with ether gives 23 g of a solid mp 208°–210° C. Recrystallization from acetone-methanol gives a white crystalline solid, mp 243°–245° C.

Anal. Calcd. for $C_9H_{14}N_4O_5$: C, 47.77; H, 6.24; N, 24.76; S, 14.17 Found: C, 47.68; H, 6.55; N, 24.39; S, 13.62.

These novel compounds possess pharmacological activity and are useful as antihypertensive agents. The compounds can be administered orally or parenterally, either alone or in association with a pharmaceutical carrier in liquid or solid dosage forms, or in combination with other drugs such as diuretics and other antihypertensives.

The amount of the compound that is to be administered to control hypertension depends upon the age, weight, the frequency of administration, and the route of administration. The dosage may range from about 0.1 to about 100 mg per kg of patient body weight.

In order to determine the utility of relative diaminopyridines when used in a method for lowering blood pressure, the oral antihypertensive activity was tested for in spontaneously (416B) and renal (416J) hypertensive rats.

The minimal p.o. hypotensive dose to lower the blood pressure of spontaneously hypertensive rats was determined to be about 1.0 mg/kg of body weight.

In an experiment to show the antihypertensive effect of chronic oral administration of compound A in spontaneously hypertensive rats, the compound was administered to separate groups of animals at 1 mg/kg of body weight twice daily for 11 consecutive days. Blood pressure was measured two hours after the first dose and then periodically throughout the test period, each measurement being made before administration of the first test dose for that day. Daily dosing produces a sustained reduction in blood pressure. In addition, a significant acute reduction in blood pressure occurs as early as two hours after the first dose.

The direct effects of several hypotensive drugs on the hindlimb vascular resistance were studied in barbiturate-anesthetized vagotomized dogs. The femoral artery was autoperfused with a Sigmamotor pump at constant blood flow. Drug-induced changes in hindlimb vascular resistance were directly proportional to changes in perfusion pressure. The test drugs were infused slowly (over 30 min) intra-arterially into the hindlimb. Compound A and minoxidil reduced hindlimb perfusion pressure thereby suggesting a direct vasodilator action on the peripheral vasculature. Perfusion pressure remained below the control level up to one hour post-infusion with each drug.

I claim:

1. A hydroxypyrimidine of the formula:

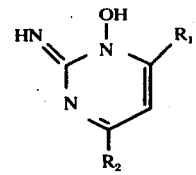

wherein $R_1$ is $CH_3$ or $-NH_2$; and wherein $R_2$ is

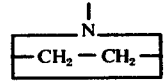

2. A hydroxypyrimidine of the formula of claim 1 wherein $R_1$ is $-NH_2$.

3. A method for producing an antihypertensive effect in a mammal suffering from hypertension which comprises the administration to said mammal of an antihypertensively effective amount of the hydroxypyrimidine of claim 1.

4. The method of claim 3 wherein $R_1$ is $-NH_2$ and $R_2$ is

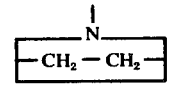

* * * * *